United States Patent
Park et al.

(10) Patent No.: US 10,980,517 B2
(45) Date of Patent: Apr. 20, 2021

(54) ULTRASONIC DIAGNOSTIC APPARATUS FOR ESTIMATING POSITION OF PROBE AND METHOD FOR CONTROLLING THE SAME

(71) Applicant: SAMSUNG MEDISON CO., LTD., Gangwon-Do (KR)

(72) Inventors: Jin Ki Park, Seoul (KR); Jong Sik Kim, Seoul (KR); Jin Yong Lee, Seoul (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 599 days.

(21) Appl. No.: 15/861,491

(22) Filed: Jan. 3, 2018

(65) Prior Publication Data

US 2018/0235580 A1    Aug. 23, 2018

(30) Foreign Application Priority Data

Feb. 23, 2017  (KR) .................. 10-2017-0024035

(51) Int. Cl.
*A61B 8/00* (2006.01)
*A61B 8/14* (2006.01)
(Continued)

(52) U.S. Cl.
CPC ............... *A61B 8/54* (2013.01); *A61B 8/145* (2013.01); *A61B 8/4245* (2013.01); (Continued)

(58) Field of Classification Search
CPC ............ G01S 15/8915; G01S 15/8936; G01S 15/8979; G01S 15/8984; G01S 15/899; (Continued)

(56) References Cited

U.S. PATENT DOCUMENTS 5,127,409 A   7/1992  Daigle
5,582,173 A   12/1996 Li
(Continued)

FOREIGN PATENT DOCUMENTS

KR  10-2013-0075472 A   7/2013
KR  10-2013-0121317 A   11/2013
KR  10-2015-0121872 A   10/2015

OTHER PUBLICATIONS

Extended European Patent Application dated Aug. 31, 2018 issued in European Patent Application No. 17206626.8.

*Primary Examiner* — Amelie R Davis
(74) *Attorney, Agent, or Firm* — Morgan, Lewis & Bockius LLP

(57) ABSTRACT

In accordance with an aspect of the present disclosure, there is provided an ultrasonic diagnostic apparatus comprise an ultrasonic probe configured to transmit an ultrasound signal to an object and receive a response signal reflected from the object, an image generator configured to create an ultrasound image of the object based on a first ultrasound signal and a first response signal and a controller configured to control transmission order and transmission intervals of the ultrasound signal and estimate a position of the ultrasonic probe based on a second ultrasound signal and a second response signal.

The ultrasonic diagnostic apparatus in accordance with embodiments of the present disclosure, the current position of the ultrasonic probe is estimated using an ultrasound signal transmitted for creation of an ultrasound image without attachment of an extra sensor, so the position of the ultrasonic probe may be estimated more economically and effectively.

14 Claims, 15 Drawing Sheets

(51) Int. Cl.
  *A61B 8/08* (2006.01)
  *G01S 15/89* (2006.01)
  *G01S 7/52* (2006.01)
  *A61B 34/20* (2016.01)

(52) U.S. Cl.
  CPC .......... *A61B 8/4254* (2013.01); *A61B 8/4444* (2013.01); *A61B 8/4488* (2013.01); *A61B 8/52* (2013.01); *A61B 8/5207* (2013.01); *G01S 7/52074* (2013.01); *G01S 15/8915* (2013.01); *G01S 15/8936* (2013.01); *G01S 15/8979* (2013.01); *G01S 15/8993* (2013.01); *A61B 8/4405* (2013.01); *A61B 8/483* (2013.01); *A61B 8/488* (2013.01); *A61B 2034/2048* (2016.02); *A61B 2034/2065* (2016.02); *G01S 7/52085* (2013.01); *G01S 15/899* (2013.01); *G01S 15/8984* (2013.01)

(58) Field of Classification Search
  CPC ............. G01S 15/8993; G01S 7/52074; G01S 7/5208; A61B 2034/2048; A61B 2034/2065; A61B 8/145; A61B 8/4245; A61B 8/4254; A61B 8/4405; A61B 8/4444; A61B 8/4488; A61B 8/483; A61B 8/488; A61B 8/52; A61B 8/5207; A61B 8/54
  See application file for complete search history.

(56) References Cited

U.S. PATENT DOCUMENTS

| | | |
|---|---|---|
| 6,364,835 B1 | 4/2002 | Hossack et al. |
| 2004/0167402 A1 | 8/2004 | Jones et al. |
| 2005/0033173 A1 | 2/2005 | Von Behren et al. |
| 2005/0113696 A1 | 5/2005 | Miller |
| 2011/0079082 A1 | 4/2011 | Yoo et al. |
| 2011/0079083 A1 | 4/2011 | Yoo et al. |
| 2012/0108972 A1 | 5/2012 | Miyama et al. |

2D Matrix

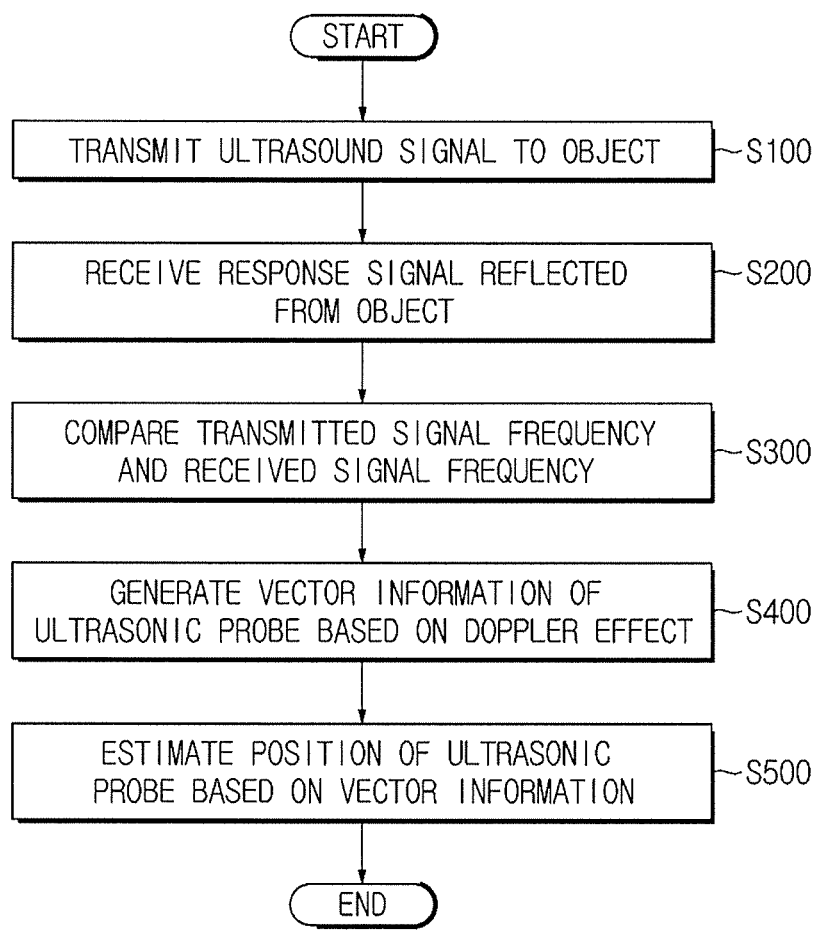

[DOPPLER EFFECT OCCURRING FROM PROBE MOTION]

[DOPPLER EFFECT OCCURRING FROM MOTION OF 2D ARRAY PROBE]

[METHOD FOR CREATING VOLUME ULTRASOUND IMAGE USING 1D ARRAY PROBE]

[METHOD FOR CREATING VOLUME ULTRASOUND IMAGE USING 1D ARRAY PROBE]

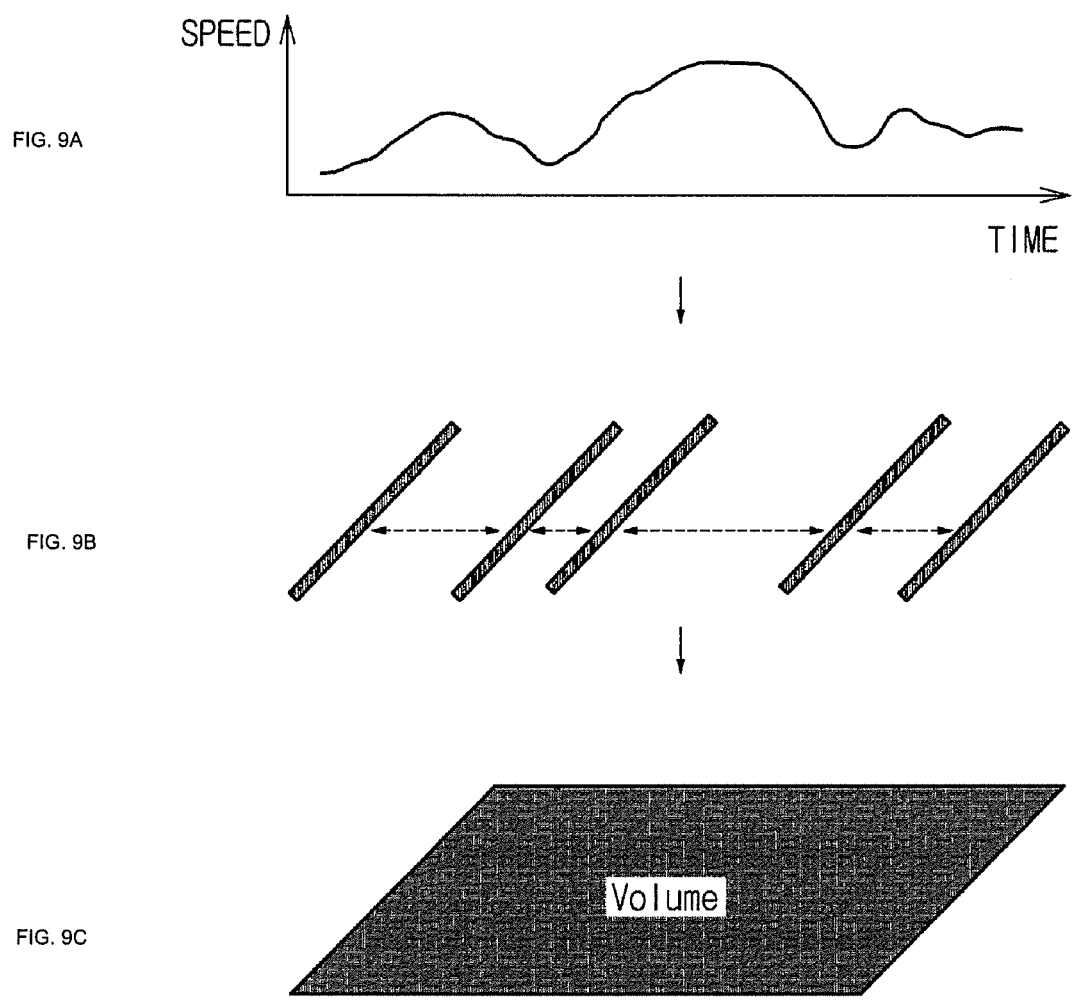
[METHOD FOR CREATING ULTRASOUND IMAGE USING 1D ARRAY PROBE]

[METHOD FOR CREATING ULTRASOUND IMAGE USING 2D ARRAY PROBE]

[METHOD FOR CREATING ULTRASOUND IMAGE USING 2D ARRAY PROBE]

Linear

2D Matrix

ULTRASONIC DIAGNOSTIC APPARATUS FOR ESTIMATING POSITION OF PROBE AND METHOD FOR CONTROLLING THE SAME

CROSS-REFERENCE TO RELATED APPLICATION

This application claims priority to and the benefit of Korean Patent Application No. 10-2017-0024035 filed on Feb. 23, 2017, the disclosure of which is incorporated herein by reference in its entirety.

BACKGROUND

1. Field of the Invention

The present disclosure relates to an ultrasonic diagnostic apparatus and method for controlling the same, and more particularly, to a technology for estimating a current position of an ultrasonic probe using an ultrasound signal transmitted to an object and its response signal to create an ultrasound image.

2. Discussion of Related Art

Ultrasonic diagnostic equipment refers to a device that irradiates ultrasound signals toward a particular region of an object, receives ultrasound signals bouncing back from the object, and noninvasively obtains a cross-sectional tomogram of a soft tissue or an image of the blood flow using the information about the reflected ultrasound signal (or ultrasonic echo signal).

The ultrasonic diagnostic equipment has advantages of being relatively compact and inexpensive over the other imaging diagnostic equipments, such as the X-ray diagnostic device, the X-ray Computerized Tomography (CT) scanner, the Magnetic Resonance Image (MRI) device, the nuclear medicine diagnostic device, etc. The ultrasonic diagnostic equipment is able to obtain an image of an internal part of the object in real time, and has high stability because of no radiation exposure. Accordingly, in general, the ultrasonic diagnostic equipment is widely used for examination in cardiology, abdomen, urology, and women clinics.

The ultrasound diagnostic apparatus includes an ultrasonic probe for transmitting ultrasounds to an object and receiving a response signal bouncing back from the object to obtain an ultrasound image of the internal part of the object.

The ultrasonic probe includes a piezo-electric layer having a piezo-electric material therein to make conversions between an electric signal and an acoustic signal while vibrating, a matching layer enabling an ultrasound produced in the piezo-electric layer to be effectively delivered to the object by reducing a difference in acoustic impedance between the piezo-electric layer and the object, a lens having an ultrasound propagating forward from the piezo-electric layer focused at a particular point, and a sound-absorbing layer for blocking the ultrasound from propagating backward from the piezo-electric layer to prevent image distortion.

As for a method for creating an ultrasound image, a technology to estimate a current position of the ultrasound is required. For the conventional ultrasonic diagnostic equipment, there is a technology to estimate a position of the ultrasonic probe with a separate position sensor, a guide, or other components attached to the ultrasonic probe.

In the case of the conventional technology, however, attaching the separate device to the ultrasonic probe to estimate the position of the ultrasonic probe increases the costs and has difficulty in creating images if the ultrasonic probe is a one dimensional (1D) array probe.

SUMMARY OF THE INVENTION

To solve the aforementioned problem, the present disclosure provides more economical and more efficient ultrasonic diagnostic apparatus and method for controlling the same, by estimating the position of the ultrasonic probe using an ultrasound signal to be transmitted for creation of an ultrasound image without having an extra sensor attached thereto.

In accordance with an aspect of the present disclosure, there is provided an ultrasonic diagnostic apparatus comprise an ultrasonic probe configured to transmit an ultrasound signal to an object and receive a response signal reflected from the object, an image generator configured to create an ultrasound image of the object based on a first ultrasound signal and a first response signal and a controller configured to control transmission order and transmission intervals of the ultrasound signal and estimate a position of the ultrasonic probe based on a second ultrasound signal and a second response signal.

The controller is may transmit the first ultrasound signal and the second ultrasound signal at different times.

The controller may estimate a position of the ultrasonic probe based on a change in frequency between the second ultrasound signal and the second response signal.

The controller may estimate a relative speed of the ultrasonic probe based on a change in frequency between the second ultrasound signal and the second response signal, and estimate a position of the ultrasonic probe based on the relative speed.

The controller may estimate a position of the ultrasonic probe based on the Doppler effect occurring between the second ultrasound signal and the second response signal.

The controller may create vector information of the ultrasonic probe based on the second ultrasound signal and the second response signal, and estimate a position of the ultrasonic probe based on the vector information.

The first and second ultrasound signals may include at least one of a brightness mode (B mode) image signal, a Doppler image signal, and a three dimensional (3D) image signal.

The controller may estimate a position of the ultrasonic probe based on an angle formed between the ultrasonic probe and the object and an angle of transmission of the second ultrasound signal.

The ultrasonic diagnostic apparatus may further include a first adjuster configured to adjust an angle formed between the ultrasonic probe and the object.

The ultrasonic diagnostic apparatus may further include a second adjuster configured to adjust an angle of transmission of the ultrasound signal.

The ultrasonic diagnostic apparatus may further include a sensor configured to detect operation information about the ultrasonic probe, wherein the controller may estimate a position of the ultrasonic probe based on the operation information.

The sensor may include at least one of a position sensor, an angle sensor, a gyro sensor, an acceleration sensor, an acoustic sensor, a photo sensor, and a magnetic sensor.

The ultrasonic probe may include a one dimensional (1D) array ultrasonic probe or a two dimensional (2D) ultrasonic probe.

The second ultrasound signal may include a plurality of second ultrasound signals with different angles, and the controller may estimate a position of the ultrasonic probe based on the plurality of second ultrasound signals and a plurality of second response signals reflected from the object.

The ultrasonic diagnostic apparatus may further include a volume image generator configured to create a volume image or panoramic image of the object based on the estimated position of the ultrasonic probe and the ultrasound image.

In accordance with another of the present disclosure, there is provided a method for controlling an ultrasonic diagnostic apparatus, the method may include transmitting an ultrasound signal to an object and receiving a response signal reflected from the object, creating an ultrasound image of the object based on a first ultrasound signal and a first response signal and estimating a position of the ultrasonic probe based on a second ultrasound signal and a second response signal.

The transmitting of an ultrasound signal to an object may include transmitting the first ultrasound signal and the second ultrasound signal at different times.

The estimating of a position of the ultrasonic probe may include estimating a relative speed of the ultrasonic probe based on a change in frequency between the second ultrasound signal and the second response signal, and estimating a position of the ultrasonic probe based on the relative speed.

The estimating of a position of the ultrasonic probe may include estimating a position of the ultrasonic probe based on the Doppler effect occurring between the second ultrasound signal and the second response signal.

The estimating of a position of the ultrasonic probe may include estimating a position of the ultrasonic probe based on an angle formed between the ultrasonic probe and the object and an angle of transmission of the second ultrasound signal.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which:

FIG. 4 is a flowchart illustrating operation of an ultrasonic diagnostic apparatus, according to an embodiment of the present disclosure;

FIGS. 8, and 9A-9C show a method for creating an ultrasound image using a 1D array ultrasonic probe, according to an embodiment of the present disclosure;

DETAILED DESCRIPTION OF EXEMPLARY EMBODIMENTS

Embodiments and features as described and illustrated in the present disclosure are only preferred examples, and various modifications thereof may also fall within the scope of the disclosure.

The terminology used herein is for the purpose of describing particular embodiments only and is not intended to limit the present disclosure. It is to be understood that the singular forms "a," "an," and "the" include plural references unless the context clearly dictates otherwise.

It will be further understood that the terms "include", "comprise" and/or "have" when used in this specification, specify the presence of stated features, integers, steps, operations, elements, and/or components, but do not preclude the presence or addition of one or more other features, integers, steps, operations, elements, components, and/or groups thereof.

It will be understood that, although the terms first, second, third, etc., may be used herein to describe various elements, components, regions, layers and/or sections, these elements, components, regions, layers and/or sections should not be limited by these terms.

Embodiments of the present disclosure will now be described in detail with reference to accompanying drawings to be readily practiced by an ordinary skill in the art.

Figure 1:
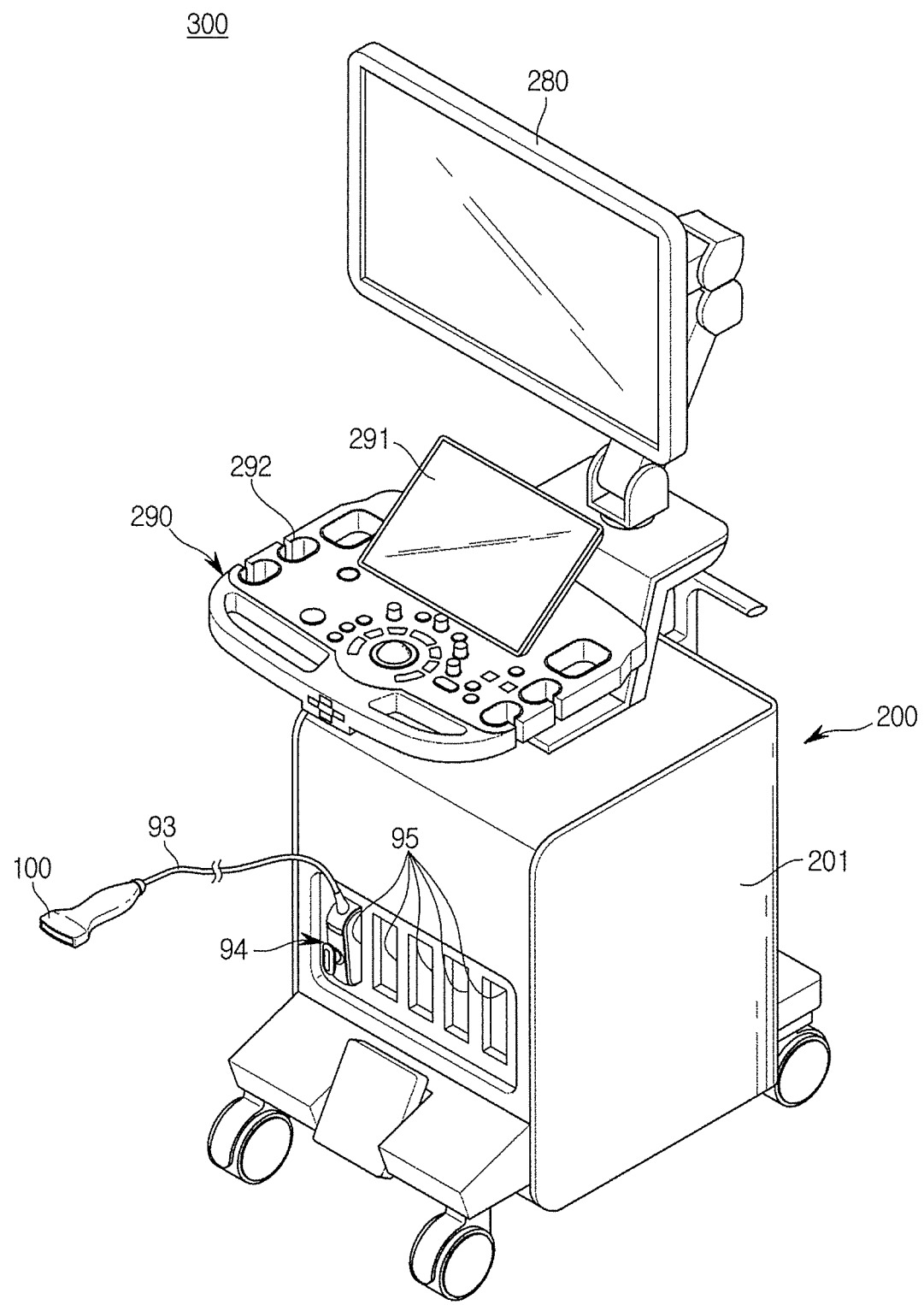
FIG. 1 is a perspective view of the appearance of an ultrasonic diagnostic apparatus, according to an embodiment of the present disclosure.
Figure 2:
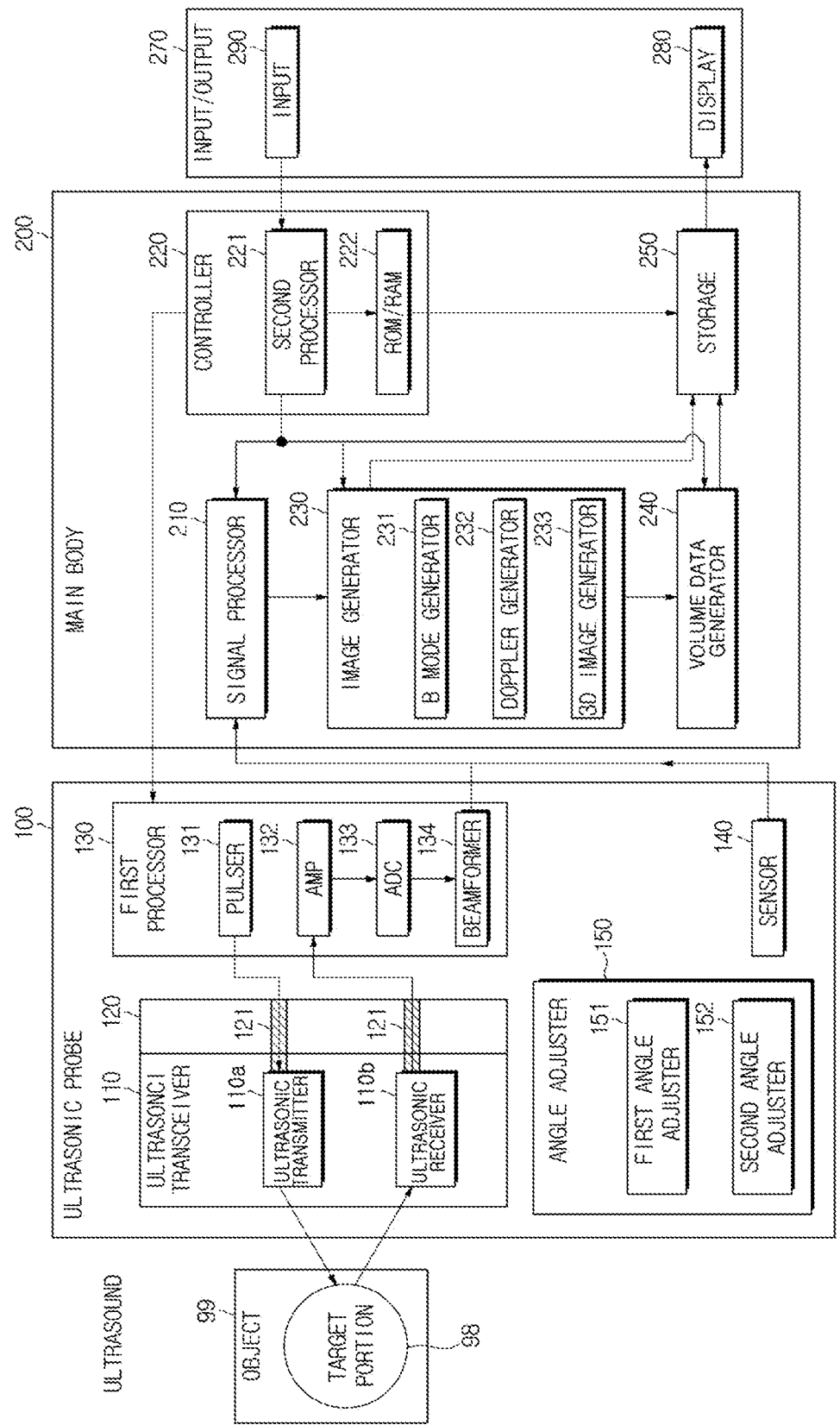
FIG. 2 is a block diagram of the internal configuration of an ultrasonic diagnostic apparatus, according to an embodiment of the present disclosure.
Figure 3A:
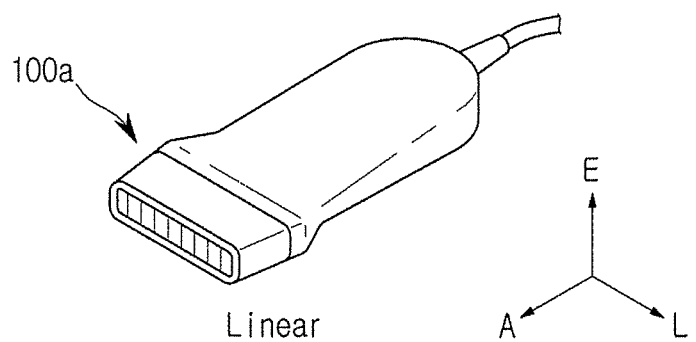
FIG. 3 is a perspective view of the appearance of various types of ultrasonic probes, according to an embodiment of the present disclosure.
Figure 3B:
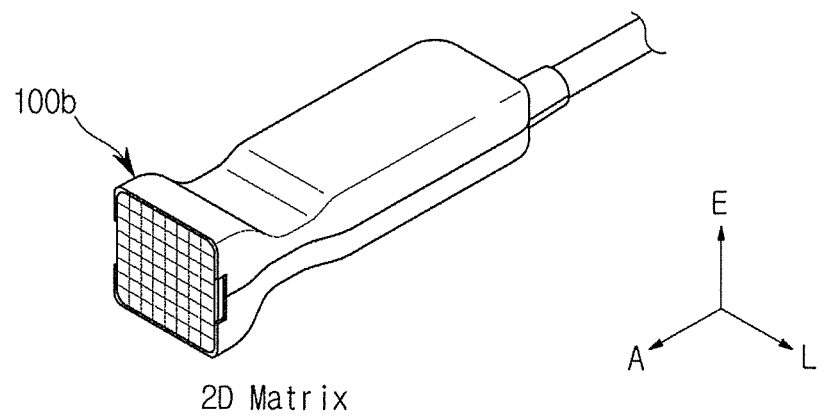

FIG. 1 is a perspective view of an ultrasonic diagnostic apparatus 300 with an ultrasonic probe 100, according to an embodiment of the present disclosure, FIG. 2 is a block diagram for explaining elements of the ultrasonic diagnostic apparatus 300, and FIG. 3 shows different types of ultrasonic probes 100 classified by the arrangement of transducers of the ultrasonic probe 100.

Referring to FIGS. 1 and 2, the ultrasonic diagnostic apparatus 300 may include a main body 200, an input 290 for receiving instructions from the user to control the ultrasonic diagnostic apparatus 300, and a display 280 for outputting information received from the input 290 and the main body 200.

Specifically, the main body 200 may control general operation of the ultrasonic diagnostic apparatus 300, and accordingly, may be equipped with various parts to control overall operation of the ultrasonic probe 100 or the main body 200. The main body 200 and the ultrasonic probe 100 may exchange data using a cable 93 or a wireless communication module.

Furthermore, the ultrasound probe 100 and the main body 200 may be connected to be able to communicate with each other using the connection cable 93, as shown in FIG. 1. An electric signal output from the ultrasonic probe 100 may be sent to the main body 200 through the connection cable 93. A control command created by the main body 200 may also be sent to the ultrasonic probe 100 through the connection cable 93.

One end of the connection cable 93 may be attached to a connector 94, which may be connected to and disconnected from a port 95 located on an outer case 201 of the main body 200. While the connector 94 is connected to the port 95, the ultrasonic probe 100 and the main body 200 may be communicatively connected.

On a side of the main body 200, a probe holder 292 may be arranged to hold the ultrasonic probe 100. The probe holder 292 may be provided as many as the number of the ultrasonic probes 100, and detachably attached to the main body 200. When not using the ultrasonic probe 100, the user may hang the ultrasonic probe 100 on the probe holder 293.

Furthermore, the main body 200 may receive an electric signal output from the ultrasonic probe 100 over a wireless communication network, and send an electric signal generated by the main body 200 to the ultrasonic probe 100. In this case, the ultrasonic probe 100 and the main body 200 may each have a wireless communication module including an antenna and a wireless communication chip.

The wireless communication module may be a short-range communication module using at least one of Bluetooth, Bluetooth low energy, infrared data association (IrDA), wireless fidelity (Wi-Fi), Wi-Fi Direct, Ultra-Wideband (UWB), and Near Field Communication (NFC), or a radio communication module supporting ITU-authorized 3GPP family, 3GPP2 family, or IEEE family.

The main body 200 may exchange data with a hospital server or another medical equipment in the hospital connected through the Picture Archiving and Communication System (PACS) through the communication unit. Furthermore, the main body 200 may exchange data according to the Digital Imaging and Communications in Medicine (DICOM) standard. However, it is not limited thereto.

The display 280 may be combined with the main body 200 and may output various kinds of information received from the main body 200.

Specifically, the display 280 may display an ultrasound image of a target part inside an object. The ultrasound image displayed on the display 280 may be a two dimensional (2D) or three dimensional (3D) ultrasound image, or a Doppler image, and various ultrasound images may be displayed according to operating modes of the ultrasonic diagnostic apparatus 300.

In an embodiment, the ultrasound image may include an Amplitude mode (A-mode) image, Brightness Mode (B-mode) image, Motion mode (M-mode) image, and further include a Color mode (C-mode) image and Doppler mode (D-mode) image.

An A-mode image refers to an ultrasound image representing an amplitude of an ultrasound signal corresponding to an echo ultrasound signal; a B-mode image refers to an ultrasound image representing a magnitude of an ultrasound signal corresponding to an echo ultrasound signal by a brightness level; and an M-mode image refers to an ultrasound image representing movements of the object over time at a particular position. A D-mode image refers to an ultrasound image representing a moving object in waveforms by means of the Doppler effect, and a C-mode image refers to an ultrasound image representing a moving object in a color spectrum.

Accordingly, the display 280 may be implemented in various well-known methods, with Cathode Ray Tube (CRT), Liquid Crystal Display (LCD), Light Emitting Diodes (LEDs), Plasma Display Panel (PDP), Organic Light Emitting Diodes (OLEDs), etc. The input 290 may be implemented in various ways, e.g., with a keyboard, a foot switch, or a foot pedal.

For example, the keyboard may be implemented in hardware. The keyboard may include at least one of switches, keys, a joy stick, and a trackball, or may be implemented in software such as a graphic user interface (GUI). In this case, the keyboard may be displayed by the main display 280.

In a case that the display 280 is implemented in a type of touch screen, the display 280 may serve as the input unit 290 as well. The main unit 200 may receive various commands from the user through at least one of the display 280 and the input unit 290. In an embodiment, a third display 291 shown in FIG. 1 may have both display and input functions.

Given that the display 280 and the input 290 receive or send information to the user, the display 280 and the input 290 may be collectively defined as an input/output unit 270.

The main body 200 of the ultrasonic diagnostic apparatus 300 has thus far been examined in connection with FIG. 1. Configurations and types of the ultrasonic probe 100 will now be described with reference to FIGS. 2 and 3.

Referring to FIG. 2, the ultrasonic probe 100 may include an ultrasonic transceiver 110 for generating or receiving ultrasounds, a first processor 130 electrically connected to the ultrasonic transceiver 110 for controlling operation of the ultrasonic transceiver 110 or performing signal processing with an electric signal output from an ultrasonic element, a sensor 140 for detecting information about operation of the ultrasonic probe 100, a first angle adjuster 151 for adjusting an angle formed between the ultrasonic prove 100 and an object 99, and a second angle adjuster 152 for adjusting an angle of transmission of an ultrasound signal.

The ultrasonic transceiver 110 may include ultrasonic transducers for generating an ultrasound or an electric signal corresponding to an ultrasound. Specifically, the ultrasonic transducer may generate an ultrasound by converting alternate current (AC) energy with a certain frequency into mechanical vibrations with the same frequency, or convert mechanical vibrations with a certain frequency caused by a received ultrasound to AC energy. That is, the ultrasonic transducer may generate an ultrasound or may output an electric signal corresponding to an ultrasound.

Referring to FIG. 2, the ultrasonic transceiver 110 may include an ultrasonic transmitter 110a and an ultrasonic receiver 110b.

The ultrasonic transmitter 110a may generate an ultrasound with a frequency corresponding to a frequency of a pulse signal sent from the first processor 130 or the second processor 220. The ultrasound may be irradiated to a target portion 98 of the object 99.

The ultrasonic receiver 110b may receive an ultrasound bouncing back from the target portion 98 of the object 99 or an ultrasound generated at the target portion 98 from e.g., a laser, and convert the received signal to an ultrasound signal. The ultrasonic receiver 110b may include a plurality of ultrasonic transducers, each of which outputs an ultrasound signal, and may thus output ultrasound signals of a plurality of channels.

Furthermore, the ultrasonic receiver 110b may be installed on one side of an acoustic absorber 120, and the acoustic absorber 120 may have a first connector 121 for the ultrasonic transceiver 110.

In an embodiment, the first connector 121 may be installed in the acoustic absorber 120 by passing through the acoustic absorber 120, in which case the first connector 121 may be installed by even penetrating the other side of the acoustic absorber 120.

The first processor 130 may generate and output an electric signal to control the ultrasonic transceiver 110, or use an ultrasound signal sent from the ultrasonic transceiver 110 to perform various kinds of signal processing.

The electric signal output from the first processor 130 may be sent to the ultrasonic transceiver 110, e.g., the ultrasonic transmitter 110a, through the first connector 121. The ultrasonic transmitter 110a may operate in response to the received electric signal.

In the embodiment of FIG. 2, the first processor 130 may include at least one of a pulser 131, an amplifier (AMP) 132, an analog-digital converter (ADC) 133, and a beamformer (or B.F.) 134.

The pulser 131 may generate voltage with a certain frequency to operate the ultrasonic transceiver 110 and send the voltage to the ultrasonic transceiver 110. The ultrasonic transceiver 110 may generate an ultrasound by vibrating according to the amplitude and frequency of the voltage output from the pulser 131.

A frequency and intensity of the ultrasound generated by the ultrasonic transceiver 110 may be determined based on the amplitude and frequency of the voltage generated by the pulser 131. The voltage output from the pulser 131 may be applied to the ultrasonic transceiver 110 at certain intervals, and accordingly, the ultrasound generated by the ultrasonic transceiver 110 may be focused at the target portion 98 or steered to a certain direction.

In some embodiments, the pulser 131 may be included in the second processor 221. In this case, the first processor 130 may not include the pulser 131.

The AMP 132 may amplify the ultrasound signal output from the ultrasonic receiver 110b of the ultrasonic transceiver 110. In some embodiments, the amplifier 132 may compensate for dynamic differences between ultrasound signals of the plurality of channels by differently amplifying the ultrasound signals of the plurality of channels output from the plurality of ultrasonic transceivers 110.

The ADC 133 may convert an amplified analog ultrasound signals to a digital signal. The ADC 133 may sample the analog ultrasound signal at a predetermined sampling rate to output the digital signal.

The beamformer 134 may focus the ultrasound signals input on the plurality of channels into a beam. The beamformer 134 may focus the signals sent from the ultrasonic transceiver 110, the AMP132, or the ADC 133 to produce a beamformed signal. The beamformer 134 may perform electronic beam scanning, steering, focusing and apodizing on the signals of the plurality of channels.

Furthermore, if the ultrasonic probe 100 is a wireless ultrasonic probe, it may be further equipped with a battery (not shown) to supply power to the ultrasonic probe 100.

The sensor 140 is attached onto a side of the ultrasonic probe 100 to detect many different kinds of operation information of the ultrasonic probe 100.

Specifically, the sensor 140 may include at least one of a position sensor, an angle sensor, a gyro sensor, an acceleration sensor, an acoustic sensor, a photo sensor, and a magnetic sensor, and the many different kinds of operation information of the ultrasonic probe 100 obtained from the enumerated sensors may be basic information for the controller 220 to estimate a position of the ultrasonic probe 100.

The angle adjuster 150 may include a first angle adjuster 151 and a second angle adjuster 152.

Specifically, the first angle adjuster 151 may adjust an angle formed between the ultrasonic probe 100 and the object 99, and the second angle adjuster 152 may adjust an angle of transmission of an ultrasound transmitted from the ultrasonic transceiver 110.

As will be described later in connection with FIG. 8, since the position of the ultrasonic probe 100 is estimated by compensation based on the angle formed between the ultrasonic probe 100 and the object 99 in the embodiment of the present disclosure, the first angle adjuster 151 may adjust the angle formed between the ultrasonic probe 100 and the object 99 and the second angle adjuster 152 may adjust the angle of an ultrasound signal to be transmitted by the ultrasonic transceiver 110 to the object 99.

Furthermore, the first angle adjuster 151 may be further equipped with a fixer (not shown) to fix the ultrasonic probe 100 and the object 99 to form a constant angle.

As shown in FIG. 2, the main body 200 may include a signal processor 210, an image generator 230, a volume data generator 240, a storage 250, and a controller 220.

The signal processor 210 may perform various signal processing on the beamformed signal. For example, the signal processor 210 may perform at least one of a filtering process, a detection process, and a compression process. The filtering process is a process to eliminate other signals than a signal in a particular bandwidth by applying a filter to the beamformed signal. The filtering process may include a harmonic imaging process to eliminate fundamental frequency components while passing harmonic signals. The detection process is a process to transform the voltage of an ultrasound signal from a radio frequency format to a video signal format. The compression process is a process to reduce the difference in amplitude between ultrasound signals. The image generator 230 may be omitted as needed.

The image generator 230 may convert a beamformed signal or a signal processed by the signal processor 210 to an ultrasound image in the format of a still image or moving image, and if needed, may process image processing on the still image or the moving image.

The image generator 230 may generate an ultrasound image using scan conversion. The ultrasound image may include an A mode image, a B mode image, an M mode image, a D mode image, or a 3D image. The ultrasound image may include the D image formed by using the Doppler effect.

The A mode ultrasound image refers to an ultrasound image obtained by imaging the intensity of reflection in amplitudes based on a distance or time between the target portion 98 and the ultrasonic probe 100, and the B mode ultrasound image refers to an ultrasound image obtained by representing the intensity of the ultrasound by brightness. The M mode ultrasound image refers to an ultrasound image obtained by imaging an extent of change in motion of the object being imaged. The D image may include a bloodstream Doppler image (also referred to as a color Doppler image), a tissue Doppler image that represents movement of tissues, or a spectral Doppler image that represents the moving speed of the object in a waveform.

Accordingly, the B mode generator 231 may extract B mode components from ultrasound data and generate an ultrasound image by representing the intensity of the signal in brightness based on the extracted B mode components.

Similarly, the Doppler generator 232 may extract Doppler components from the ultrasound data, and may generate a D image that represents a motion of the object in colors or waveforms based on the Doppler components.

The image generator 230 may also correct the generated ultrasound image. For example, the image generator 230 may correct brightness, luminosity, sharpness, contrast, color or the like of an entire or a part of the ultrasound image in order for the user to clearly view tissues in the ultrasound image. As needed, the image generator 230 may cancel noise in the ultrasound image or perform pixel interpolation.

The image generator 230 may send the generated or corrected ultrasound image to the storage 250, or display the ultrasound image on the display 280. The image generator 230 may also send the generated or corrected ultrasound image to the volume data generator 240 to obtain ultrasound volume data.

The volume data generator 240 may obtain ultrasound volume data representing a 3D volume based on the generated or corrected 2D ultrasound image.

The signal processor 210, the image generator 230, and the volume data generator 240 may be implemented by a central processing unit (CPU) or a graphic processing unit (GPU). The CPU or GPU may be implemented with at least one semiconductor chip and associated components.

The storage 250 may store various programs or data related to functions of the controller 220, ultrasound images, and various kinds of information regarding the ultrasound images. The storage 250 may be implemented using a semiconductor storage device, a magnetic disk storage device, or a magnetic tape storage device.

The controller 220 may control overall operations of the ultrasound diagnostic apparatus 300 in accordance with commands from the user or predefined settings. For example, the controller 220 may generate a control command based on the frequency of an ultrasound to be irradiated, and send the control command to the pulser 131 of the first processor 13, which may in turn, apply a voltage with a certain frequency to the ultrasonic transceiver 110 according to the control command. Accordingly, the ultrasonic transceiver 110 may be able to generate and irradiate an ultrasound with the certain frequency to the target portion 98 of the object 99.

The controller 220 may include a read only memory (ROM) or random access memory (RAM) to assist in the second processor 221 and operation of the second processor 221. The second processor 221 may be implemented by a CPU. The CPU may be implemented with one or more semiconductor chips and associated components.

FIG. 3 shows different types of ultrasonic probes 100 classified by the shape of the ultrasonic transceiver 110 of the ultrasonic probe 100.

The ultrasonic probe 100a shown in (a) of FIG. 3 is a linear probe, in which case, transducers are arranged in a straight line.

A probe shown in (b) of FIG. 3 is a 2D matrix array ultrasonic probe 100b, which may provide a stereoscopic 360 degree image of the object, which is an ultrasonic diagnostic image.

However, the ultrasonic probe 100 is not limited thereto, and may be implemented in other forms than those shown in FIG. 3, which are known to an ordinary skill in the art, such as a phased array probe, a 3D matrix probe, etc.

Meanwhile, three directions may be defined: axial direction A, lateral direction L, and elevation direction E, which are perpendicular to each other with respect to the probe 100. Specifically, the axial direction A may be defined to be a direction in which an ultrasound signal is irradiated; the lateral direction L may be defined to be a direction in which the transducers are arranged, i.e., a direction of a row of the transducers; and the elevation direction E may be defined to be a direction perpendicular to the axial direction A and the lateral direction L.

External and internal configurations of the ultrasonic probe 100 and the ultrasonic diagnostic apparatus 300 have thus far been described. Operations flows of the present disclosure will now be described.

Figure 5:
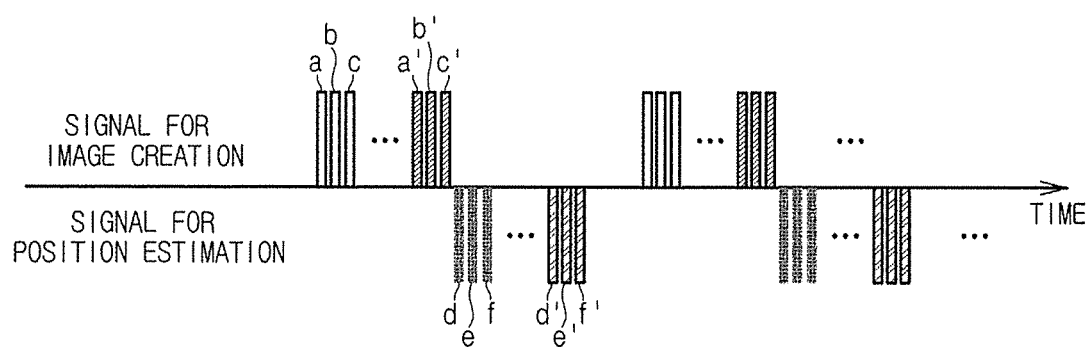
FIG. 5 shows transmission order and transmission scheme of ultrasound signals, according to an embodiment of the present disclosure.
Figure 6A:
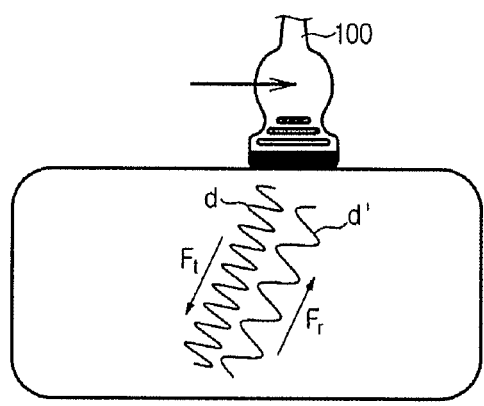
FIGS. 6A-6D show the Doppler effect from the use of one dimensional (1D) array ultrasounds, according to an embodiment of the present disclosure.
Figure 6B:
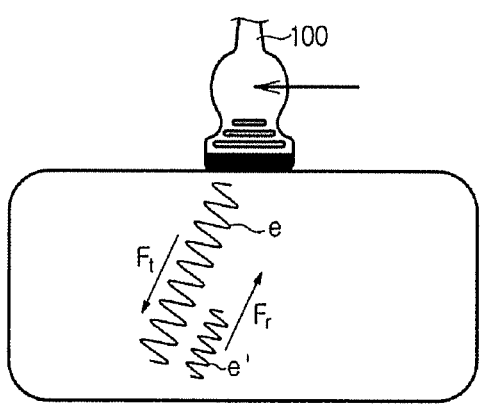
Figure 6C:
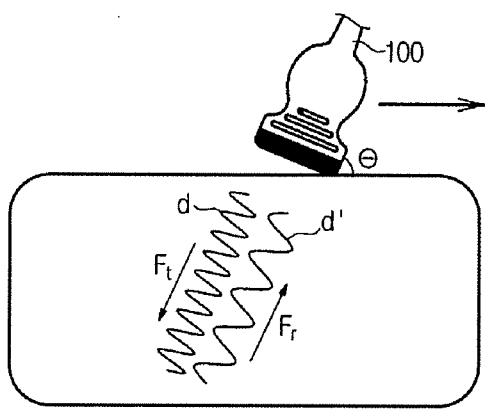
Figure 6D:
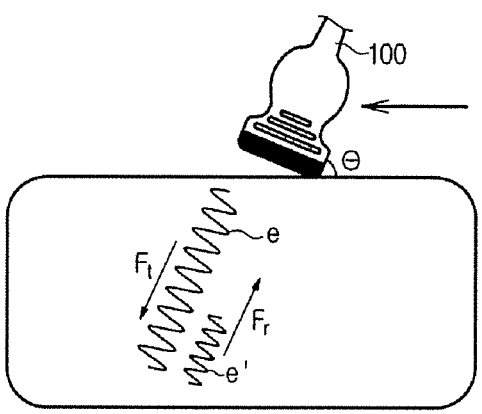
Figure 7A:
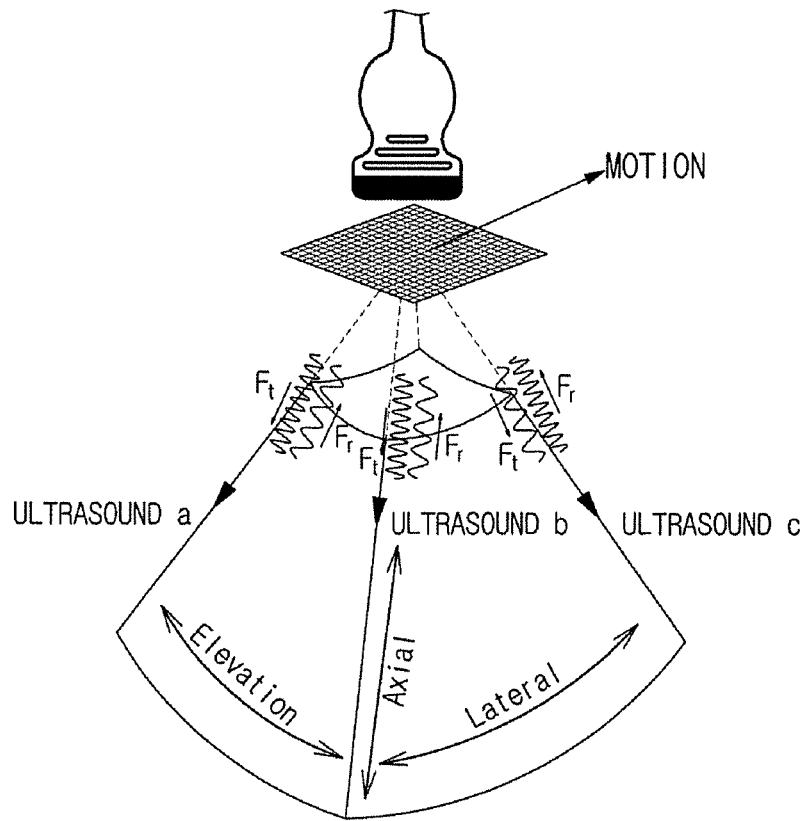
FIGS. 7A and 7B show the Doppler effect from the use of two dimensional (2D) array ultrasounds, according to an embodiment of the present disclosure.
Figure 7B:
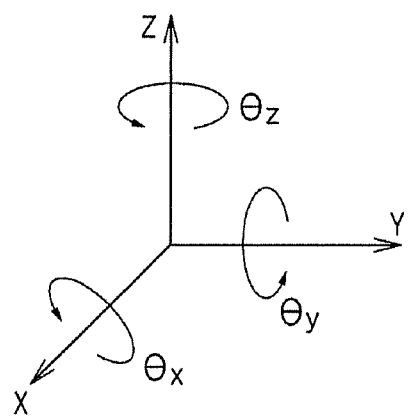

FIG. 4 is a flowchart illustrating operation of an ultrasonic diagnostic apparatus, according to an embodiment of the present disclosure, FIG. 5 shows transmission order and transmission scheme of ultrasound signals, according to an embodiment of the present disclosure, FIGS. 6A-6D show the Doppler effect from the use of 1D array ultrasounds, according to an embodiment of the present disclosure, and FIGS. 7A and 7B show the Doppler effect from the use of 2D array ultrasounds, according to an embodiment of the present disclosure.

Referring to FIG. 4, the ultrasonic probe 100 of the ultrasonic diagnostic apparatus 300 transmits ultrasounds to the object and receives a response signal bouncing back from the object, S100, S200.

The ultrasonic transceiver 110 may transmit and receive ultrasound signals toward and from the object 99, and the signals for transmission are of the same kind but may be differently used for their purposes.

For example, in order to generate an ultrasound image, the ultrasonic transceiver 110 may transmit an ultrasound signal for creation of an ultrasound image, and in order to estimate a position of the ultrasonic probe 100, the ultrasonic transceiver 110 may transmit an ultrasound signal for estimation of a position to the object 99.

In the following description, a signal to be transmitted by the ultrasonic transceiver 110 to the object 99 for creation of an ultrasound image will be called a first ultrasound signal, and the signal bouncing back from the object 99 will be called a first response signal; a signal to be transmitted by the ultrasonic transceiver 110 to the object 99 for estimation of a position of the ultrasonic probe 100 will be called a second ultrasound signal, and the signal bouncing back from the object 99 will be called a second response signal.

For example, to generate a B mode image, the ultrasonic transceiver 110 may generate a B mode transmission signal, transmit the first ultrasound signal obtained by converting the B mode transmission signal to an ultrasound signal to the object 99, and receive the first response signal bouncing back from the object 99, and based on which, the image generator 230 may generate a B mode image.

To generate a D image, the ultrasonic transceiver 110 may generate a D mode transmission signal, transmit the first ultrasound signal obtained by converting the D mode transmission signal to an ultrasound signal to the object 99, and receive the first response signal bouncing back from the object 99, and based on which the image generator 230 may generate a D image.

On the other hand, to estimate a position of the ultrasonic probe 100, the ultrasonic transceiver 110 may transmit the second ultrasound signal for estimation of the position of the ultrasonic probe 100 to the object 99, and receive the second response signal bouncing back from the object 99, and the controller 220 may estimate the position of the ultrasonic probe 110 based on the second ultrasound signal and the second response signal.

FIG. 5 shows transmission and reception of the first ultrasound signal and first response signal and the second ultrasound signal and second response signal.

Referring to FIG. 5, the ultrasonic transceiver 110 may transmit the first ultrasound signal (signals a, b, and c) for generation of an ultrasound image to the object 99 and receive the first response signal (signals a', b', and c') bouncing back from the object 99, and based on which, the image generator 230 may generate an ultrasound image of the object 99.

Furthermore, the ultrasonic transceiver 110 may transmit the second ultrasound signal (signals d, e, and f) for estimation of a position of the ultrasonic probe 100 to the object 99 and receive the second response signal (signals d', e', and f) bouncing back from the object 99, and the controller 220 may estimate the position of the ultrasonic probe 100 based on the second ultrasound signal and the second response signal.

However, since the ultrasonic transceiver 110 may not transmit multiple signals at the same time, the first ultrasound signal for generation of an ultrasound image and the second ultrasound signal for estimation of a position of the ultrasonic probe 100 may be transmitted and received at different times. The order and transmission intervals may be changed in various ways according to commands from the user or a use environment.

In the embodiment of the present disclosure, since the position of the ultrasonic probe 100 is estimated using an ultrasound signal to generate an image of the ultrasonic probe 100, there is no need for an extra sensor, so the costs may be reduced.

The first and second ultrasound signals are for generating an ultrasound image, and may include at least one of a B mode image signal, a D image signal, and a 3D image signal. The first and second ultrasound signals are not limited thereto, and may also include various signals as long as they may be used to generate an ultrasound image.

Once a response signal is receiving from the object 99, the ultrasonic diagnostic apparatus 300 compares the transmitted signal and the received signal, in S300.

Specifically, the ultrasonic transceiver 110 transmits the second ultrasound signal to the object 99 for estimation of a position of the ultrasonic probe 100, receives the second response signal bouncing back from the object 99, analyzes frequencies of the second ultrasound signal and the second response signal, and generate vector information about a relative position and speed of the ultrasonic probe 100 using the Doppler effect.

The Doppler effect is an effect observed when either or both of a wave source from which a wave begins and an observer who observes the wave are moving. According to the Doppler effect, the narrower the distance between the wave source and the observer is, the higher the frequency of the wave appears, and the farther the distance is, the lower the frequency appears. In the field of ultrasonics, the velocity of a blood flow or movement inside the object 99 is measured using the Doppler effect.

Referring to FIGS. 6A and 6B, if the ultrasonic probe 100 transmits the second ultrasound signal Ft to the object 99 and then makes a motion to the right, a frequency of the second response signal Fr bouncing back from the object 99 appears different from the frequency of the second ultrasound signal Ft due to the motion of the ultrasonic probe 100.

Specifically, if the ultrasonic probe 100 transmits an ultrasound signal to an object and then moves away from the object, the observed frequency of the ultrasound signal is measured as being lower due to the Doppler effect, so in the case of FIG. 6A, the frequency of the second response signal Fr received by the ultrasonic transceiver 110 is measured as being lower than the frequency of the second ultrasound signal Ft.

On the contrary, as shown in FIG. 6B, if the ultrasonic probe 100 transmits an ultrasound signal to an object and then moves closer to the object, the observed frequency of the ultrasound signal is measured as being higher due to the Doppler effect. Accordingly, in the case of FIG. 6B, the frequency of the second response signal Fr measured by the ultrasonic transceiver 110 is measured as being higher than the frequency of the second ultrasound signal Ft.

Furthermore, in the embodiment of the present disclosure, as shown in FIGS. 6C and D, even while the ultrasonic probe 100 is being moved at an angle, the motion of the ultrasonic probe 100 may be estimated. Specifically, if the angle θ formed between the object 99 and the ultrasonic probe 100 is known, the motion of the ultrasonic probe 100 may be estimated using the measurement result from the Doppler effect and the angle θ with the object 99. The ultrasonic probe 100 is often used while leaning at an angle as shown in FIGS. 6C and 6D, in which case the position of the ultrasonic probe 100 may be efficiently estimated.

FIGS. 6A-6D show an occasion when a 1D array ultrasonic probe is used, and FIGS. 7A and 7B show the Doppler effect when a 2D array ultrasonic probe is used.

In the case of the 1D array ultrasonic probe, changes in angle are made only in the lateral direction and accordingly, a 1D motion may be estimated, but in the case of using the 2D array ultrasonic probe, angles of transmission of the ultrasound signal may be adjusted not only in the lateral direction but also in the elevation direction, thus enabling estimation of a 3D motion as shown in FIGS. 7A and 7B.

In the case of using the 2D array ultrasonic probe, a plurality of ultrasound signals may be transmitted and received with respect to three axes, enabling estimation of the 3D motion of the ultrasonic probe 100 using the Doppler effect for each axis.

If the Doppler effect of an ultrasound signal is observed due to the motion of the ultrasonic probe 100, the controller 220 generates vector information of the ultrasonic probe 100 based on the Doppler effect and then estimates a current position of the ultrasonic probe 100 based on the vector information, in S400, S500.

Specifically, the ultrasonic diagnostic apparatus 300 may measure a relative speed of the ultrasonic prove 100 based on a change in frequency between the second ultrasound signal and the second response signal, and based on which, may estimate the position of the ultrasonic probe 100. The vector information may include at least one of relative position information, speed information, and acceleration information of the ultrasonic probe 100.

Figure 8A:
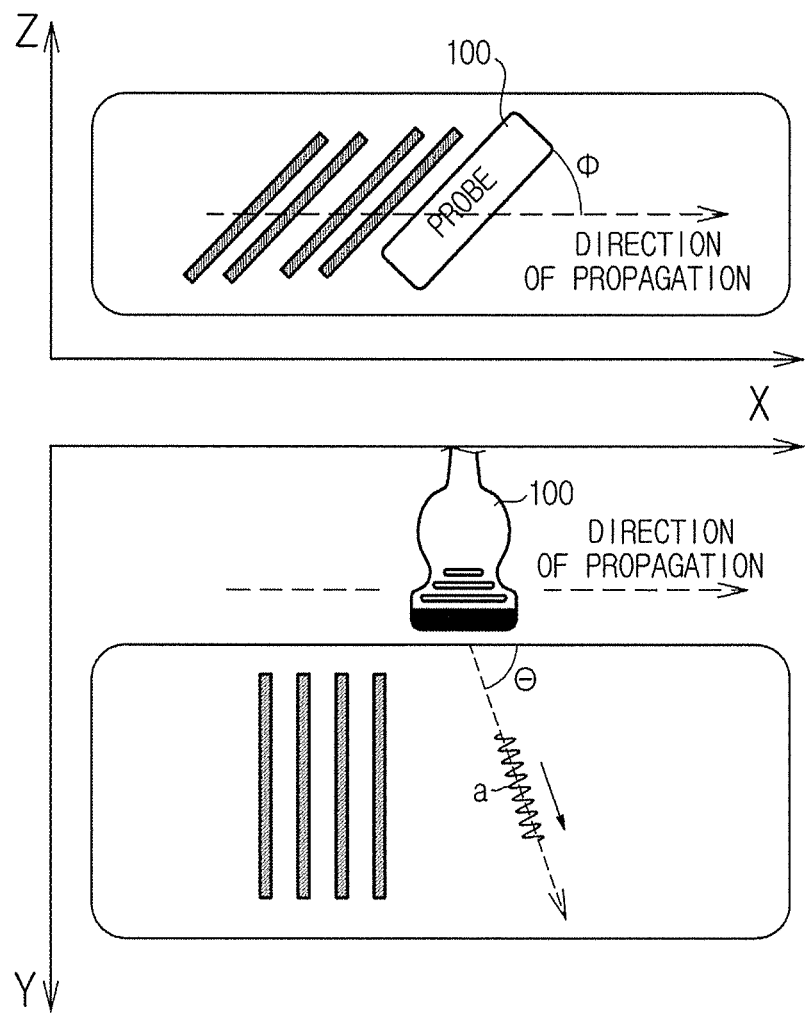
Figure 8B:
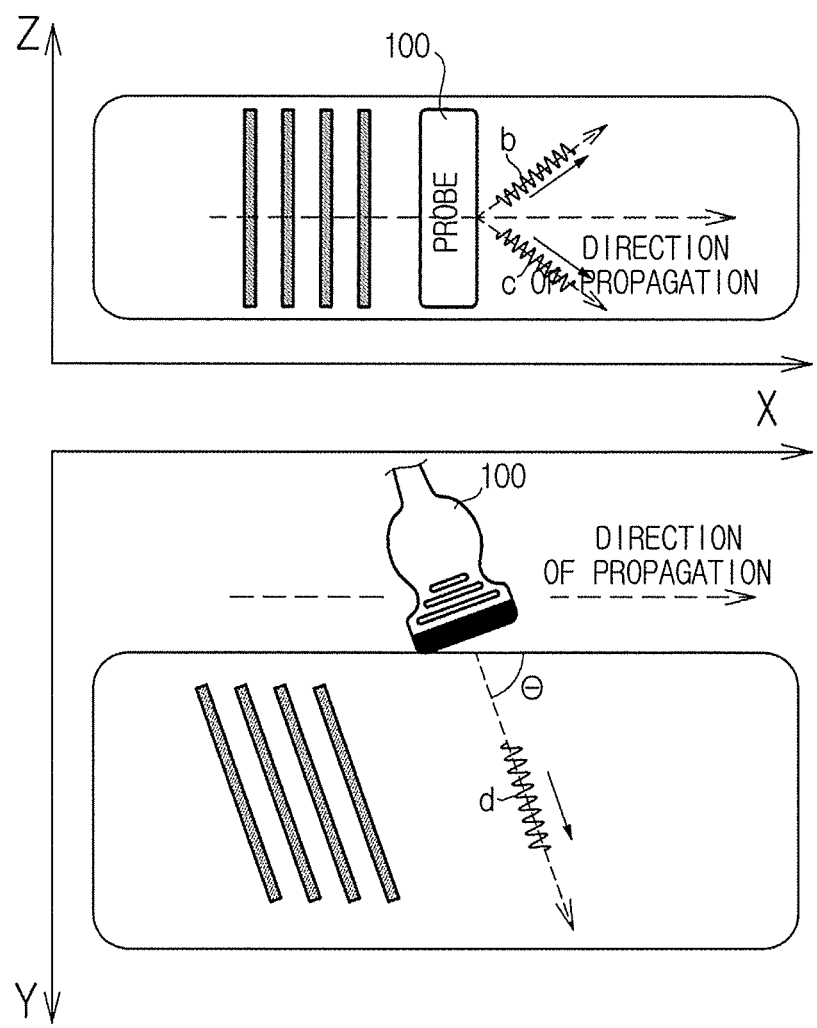

FIG. 8 shows an example of estimating a position of the ultrasonic probe 100, and FIGS. 9A-9C show a procedure of forming a freehand volume image based on the estimated position.

In the case of using the 1D array ultrasonic probe 100, it is common to observe the Doppler effect only in the lateral direction, but it is possible to estimate a motion in another direction if an angle of a motion of the ultrasonic probe 100 and an angle of transmission/reception of the ultrasound signal are already known.

For example, as shown in (a) of FIG. 8, if the ultrasonic probe 100 is moving forward while leaning at an angle (Φ) of about 45 degrees from the object 99 and an angle (θ) of transmission of a signal transmitted by the ultrasonic probe 100 to the object 99 is about 70 degrees, the speed in the moving direction may be estimated after compensation of an observed speed by 1÷(cos 45°×cos 70°)=4.13 times.

However, to estimate the position of the ultrasonic probe 100, which is the 1D array probe, the angle (θ) formed between the ultrasonic probe 100 and the object 99 and the angle (Φ) of transmission at which the ultrasonic probe 100 transmits to the object 99 need to be maintained to some extents. It is because a correct compensation value may not be calculated if the two angles become 90 degrees.

In the embodiment of the present disclosure, with the first angle adjuster 151 for adjusting the angle (θ) formed between the ultrasonic probe 100 and the object 99 and the second angle adjuster 152 for adjusting the angle of transmission (Φ) at which the ultrasonic probe 100 transmits to the object 99, the user may be able to move the ultrasonic probe 100 more easily. Furthermore, a fixer may be further included to fix the angle (θ) formed between the ultrasonic probe 100 and the object 99 and the second angle adjuster 152 for adjusting the angle of transmission (Φ) at which the ultrasonic probe 100 transmits to the object 99.

Moreover, as shown in (b) of FIG. 8, even while the ultrasonic probe 100 is being moved at an angle forward or backward, the position of the ultrasonic probe 100 may be estimated by transmitting and receiving the ultrasound signal. In this case, the 2D position and motion (to the front, back, left, right) of the ultrasonic probe 100 may be estimated using the Doppler effect occurring after two ultrasound signals (signals b and c) are transmitted and received in the left-right direction. In general, the ultrasonic probe 100 is often used while leaning forward and/or backward, and even in this case, the position of the ultrasonic probe 100 may be easily and efficiently estimated.

Once the motion of the ultrasonic probe 100 is estimated, a freehand volume as shown in FIGS. 9A-9C may be formed by determining positions of images obtained based on the motion information and adjusting the intervals. For example, after ultrasound signals are transmitted and received at regular intervals or distances, cross-sections of the ultrasound images of the object 99 are obtained, and the freehand volume image may be created based on the position of the estimated ultrasonic probe 100.

Figure 10:
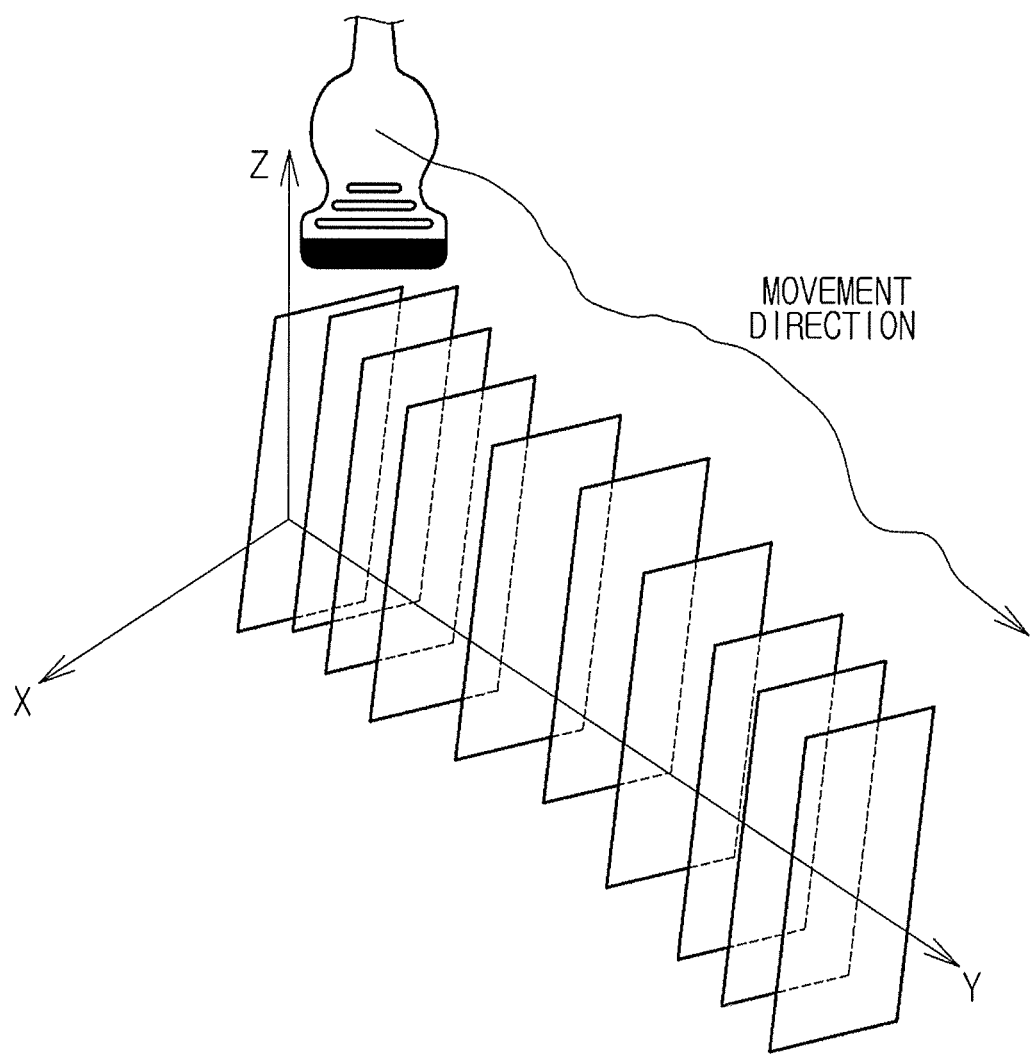
FIGS. 10 and 11 show a method for creating an ultrasound image using a 2D array ultrasonic probe, according to an embodiment of the present disclosure.
Figure 11:
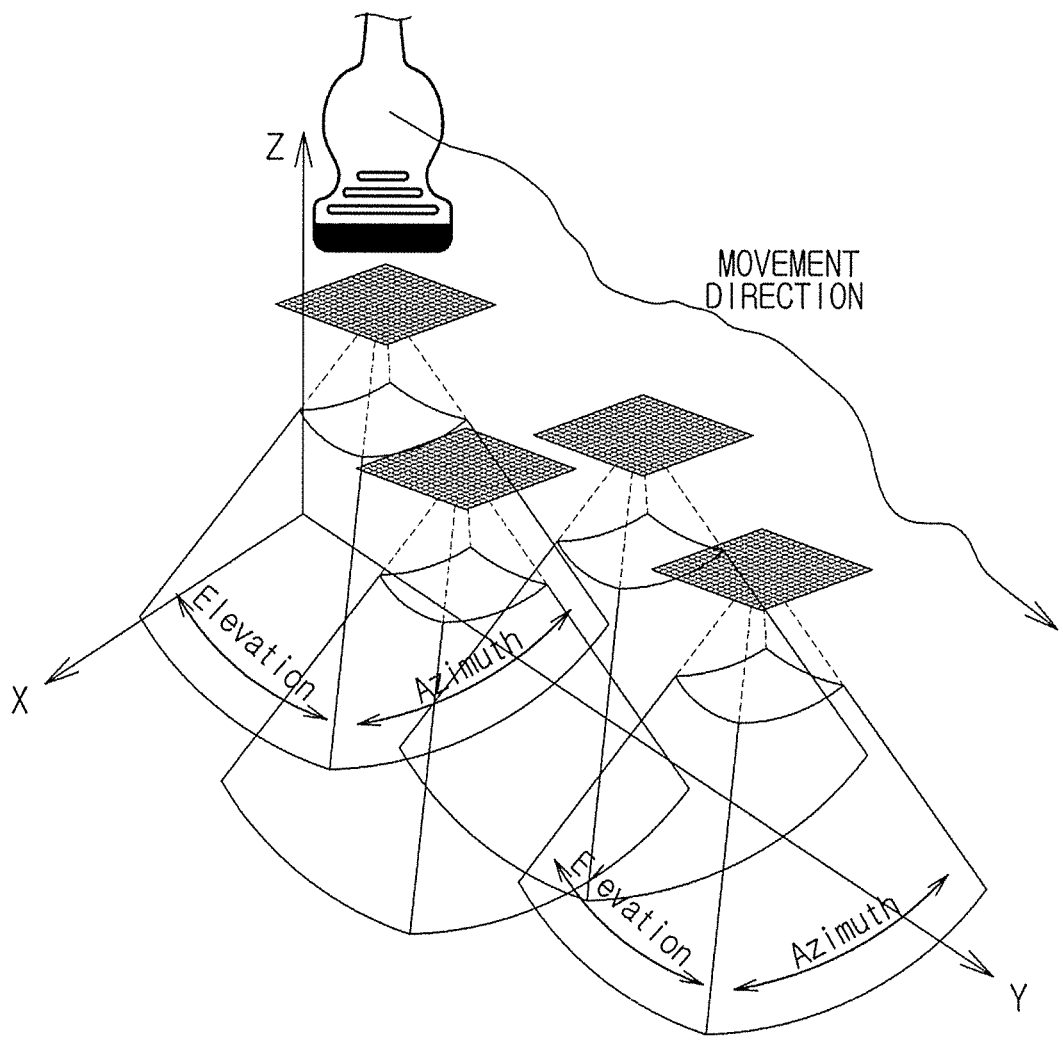

FIGS. 10 and 11 show a method for creating an ultrasound image using a 2D array ultrasonic probe, according to an embodiment of the present disclosure.

Referring to FIGS. 10 and 11, the ultrasonic probe 100 may transmit and receive ultrasound signals to and from the object 99 while moving in a certain direction. The ultrasound signals transmitted and received may be the first ultrasound signal for creation of an ultrasound image or the second ultrasound signal for estimation of a position of the ultrasonic probe 100. In other words, the ultrasonic probe 100 may obtain cross-sections of the object 99 by transmitting and receiving ultrasound signals at certain cycles or intervals, and simultaneously, estimate the current position of the ultrasonic probe 100.

After that, as shown in FIG. 11, the freehand volume image may be created based on the obtained cross-sections and estimated position of the ultrasonic probe 100.

Figure 12A:
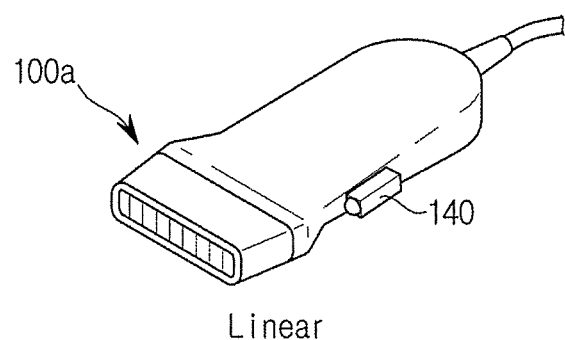
FIG. 12 shows sensor-equipped ultrasonic probes, according to an embodiment of the present disclosure.
Figure 12B:
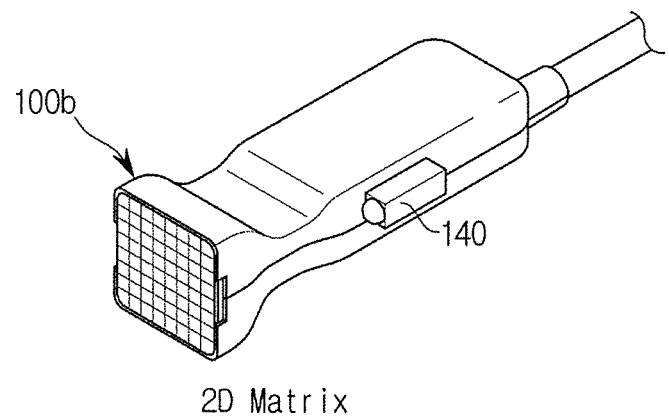

FIG. 12 shows sensor-equipped ultrasonic probes, according to an embodiment of the present disclosure.

Although the embodiment of the present disclosure may estimate the position of the ultrasonic probe 100 without attaching a sensor, a more correct position of the ultrasonic probe 100 may be estimated if the sensor 140 is attached.

The sensor 140 may include at least one of a position sensor, an angle sensor, a gyro sensor, an acceleration sensor, an acoustic sensor, a photo sensor, and a magnetic sensor, without being limited thereto. Although FIG. 12 shows the sensor 140 attached onto an external side of the ultrasonic probe 100, the position of the sensor 140 is not limited thereto but may be attached onto the inside of the ultrasonic probe 100.

Features and benefits of the present disclosure have thus far been described in connection with various embodiments of the present disclosure.

In the case of the conventional ultrasonic diagnostic apparatus, extra equipment needs to be attached to the ultrasonic probe to estimate the position of the ultrasonic probe, leading to an increase in costs, and there are many difficulties in creating an image with the 1D array probe.

However, in the case of the ultrasonic diagnostic apparatus in accordance with embodiments of the present disclosure, the current position of the ultrasonic probe is estimated using an ultrasound signal transmitted for creation of an ultrasound image without attachment of an extra sensor, so the position of the ultrasonic probe may be estimated more economically and effectively.

According to embodiments of the present disclosure, a current position of an ultrasonic probe may be estimated using an ultrasound signal to be transmitted for creation of an ultrasound image without having an extra sensor attached to the ultrasonic probe to estimate the position of the ultrasonic probe, so the position of the ultrasonic probe may be estimated more economically and effectively.

Although the present disclosure is described with reference to some embodiments as described above and accompanying drawings, it will be apparent to those ordinary skilled in the art that various modifications and changes can be made to the embodiments. For example, the aforementioned method may be performed in different order, and/or the aforementioned systems, structures, devices, circuits, etc., may be combined in different combinations from what is described above, and/or replaced or substituted by other components or equivalents thereof, to obtain appropriate results. Therefore, other implementations, other embodiments, and equivalents thereof may fall within the following claims.

What is claimed is:

1. An ultrasonic diagnostic apparatus comprising:
   an ultrasonic probe configured to:
     transmit at least one first ultrasound signal and at least one second ultrasound signal to an object, and
     receive at least one first response signal which is a reflection of the at least one first ultrasound signal from the object and at least one second response signal which is a reflection of the at least one second ultrasound signal from the object;
   an image processor configured to create an ultrasound image of the object based on the at least one first response signal; and
   a controller configured to control the ultrasonic probe to transmit the at least one first ultrasound signal and the at least one second ultrasound signal at different times,
   wherein the at least one second ultrasound signal is transmitted from the ultrasonic probe by being steered by a preset angle in a lateral direction, and
   the controller is further configured to estimate a position of the ultrasonic probe based on the preset angle and a change in frequency between the at least one second ultrasound signal and the at least one second response signal.

2. The ultrasonic diagnostic apparatus of claim 1, wherein the controller is further configured to estimate a relative speed between the ultrasonic probe and the object based on the preset angle and the change in frequency between the at least one second ultrasound signal and the at least one second response signal, and to estimate the position of the ultrasonic probe based on the relative speed between the ultrasonic probe and the object.

3. The ultrasonic diagnostic apparatus of claim 1, wherein the controller is further configured to estimate the position of the ultrasonic probe based on a Doppler effect occurring between the at least one second ultrasound signal and the at least one second response signal.

4. The ultrasonic diagnostic apparatus of claim 1, wherein the controller is further configured to create vector information of the ultrasonic probe based on the at least one second ultrasound signal and the at least one second response signal, and to estimate the position of the ultrasonic probe based on the vector information.

5. The ultrasonic diagnostic apparatus of claim 1, wherein the at least one first ultrasound signal and the at least one second ultrasound signal comprise at least one of a brightness mode (B mode) image signal, a Doppler image signal, or a three dimensional (3D) image signal.

6. The ultrasonic diagnostic apparatus of claim 1, further comprising: a sensor configured to detect operation information about the ultrasonic probe,
wherein the controller is further configured to estimate the position of the ultrasonic probe based on the operation information.

7. The ultrasonic diagnostic apparatus of claim 6, wherein the sensor comprises at least one of a position sensor, an angle sensor, a gyro sensor, an acceleration sensor, an acoustic sensor, a photo sensor, or a magnetic sensor.

8. The ultrasonic diagnostic apparatus of claim 1, wherein the ultrasonic probe comprises a one dimensional (ID) array ultrasonic probe or a two dimensional (2D) ultrasonic probe.

9. The ultrasonic diagnostic apparatus of claim 1, wherein the at least one second ultrasound signal comprises a plurality of second ultrasound signals transmitted from the ultrasonic probe by being steered by different angles, and
the at least one second response signal comprises a plurality of second response signals which are the plurality of second ultrasound signals reflected from the object, respectively.

10. The ultrasonic diagnostic apparatus of claim 1, wherein the image processor is further configured to create a volume image or panoramic image of the object based on the estimated position of the ultrasonic probe and the ultrasound image.

11. A method for controlling an ultrasonic diagnostic apparatus, the method comprising:
transmitting, by an ultrasonic probe, at least one first ultrasound signal to an object and receiving, by the ultrasonic probe, at least one first response signal which is a reflection of the at least one first ultrasound signal from the object;
transmitting, by the ultrasonic probe, at least one second ultrasound signal to the object and receiving, by the ultrasonic probe, at least one second response signal which is a reflection of the at least one second ultrasound signal from the object;
creating an ultrasound image of the object based on the at least one first response signal; and
estimating a position of the ultrasonic probe based on the at least one second ultrasound signal and the at least one second response signal,
wherein the at least one first ultrasound signal and at least one second ultrasound signal are transmitted by the ultrasonic probe at different times,
the at least one second ultrasound signal is transmitted from the ultrasonic probe by being steered by a preset angle in a lateral direction, and
the estimating of the position of the ultrasonic probe comprises estimating the position of the ultrasonic probe based on the preset angle and a change in frequency between the at least one second ultrasound signal and the at least one second response signal.

12. The method of claim 11, wherein the estimating of the position of the ultrasonic probe comprises estimating a relative speed between the ultrasonic probe and the object based on the preset angle and the change in frequency between the at least one second ultrasound signal and the at least one second response signal, and estimating the position of the ultrasonic probe based on the relative speed between the ultrasonic probe and the object.

13. The method of claim 11, wherein the estimating of the position of the ultrasonic probe comprises estimating the position of the ultrasonic probe based on a Doppler effect occurring between the at least one second ultrasound signal and the second response signal.

14. The method of claim 11, wherein the at least one second ultrasound signal comprises a plurality of second ultrasound signals transmitted from the ultrasonic probe by being steered by different angles, and
the at least one second response signal comprises a plurality of second response signals which are the plurality of second ultrasound signals reflected from the object, respectively.

* * * * *